(12) United States Patent
Buan et al.

(10) Patent No.: US 11,007,083 B2
(45) Date of Patent: May 18, 2021

(54) DRESSING

(71) Applicant: Aatru Medical, LLC, Cleveland, OH (US)

(72) Inventors: John Buan, Maple Grove, MN (US); Richard L. Middaugh, Rocky River, OH (US); Timothy Wojciechowski, Westlake, OH (US); Thomas E. Lash, Chardon, OH (US)

(73) Assignee: Aatru Medical, LLC, Cleveland, OH (US)

( * ) Notice: Subject to any disclaimer, the term of this patent is extended or adjusted under 35 U.S.C. 154(b) by 340 days.

(21) Appl. No.: 16/114,813

(22) Filed: Aug. 28, 2018

(65) Prior Publication Data
US 2020/0069479 A1  Mar. 5, 2020

(51) Int. Cl.
*A61F 13/02* (2006.01)
*A61F 13/00* (2006.01)
(Continued)

(52) U.S. Cl.
CPC .......... *A61F 13/0216* (2013.01); *A61B 46/20* (2016.02); *A61F 13/00063* (2013.01);
(Continued)

(58) Field of Classification Search
CPC ................ A61F 13/0206; A61F 13/216; A61F 13/0216; A61F 13/0276; A61F 13/0289
See application file for complete search history.

(56) References Cited

U.S. PATENT DOCUMENTS 6,008,429 A * 12/1999 Ritger ..................... A61L 15/58
                                                                 206/441
6,077,986 A *  6/2000 Hilston ............... A61F 13/0276
                                                                  602/41
(Continued)

FOREIGN PATENT DOCUMENTS

WO      WO-2012125530 A1 *  9/2012  ......... A61F 13/0246

OTHER PUBLICATIONS

Koomen, Maria; Using Polymer Solution Casting to Deliver High-Quality Films; Dec. 15, 2015 (Year: 2015).*
(Continued)

*Primary Examiner* — Catharine L Anderson
*Assistant Examiner* — Arjuna P Chatrathi
(74) *Attorney, Agent, or Firm* — Rankin, Hill & Clark LLP (57) ABSTRACT

A dressing includes a drape, a pressure-sensitive acrylic-based adhesive on a skin-facing surface of the drape, an island of absorbent material, a silicone gel backing film, a silicone gel on the silicone gel backing film, and a release liner. The drape is a thin film capable of maintaining a negative pressure underneath the drape upon application of a vacuum. The island of absorbent material has a smaller area than the drape and is applied onto the skin-facing surface of the drape. The silicone gel backing film has a frame shape and a smaller footprint than the drape and a larger footprint than the island of absorbent material. The release liner has a larger area than the drape. The release liner is coated with a fluorosilicone release coating, which is in contact with the pressure-sensitive acrylic-based adhesive on the drape and is in contact with the silicone gel.

4 Claims, 4 Drawing Sheets

(51) Int. Cl.
  *A61B 46/20* (2016.01)
  *A61L 15/42* (2006.01)
  *A61L 15/58* (2006.01)
  *A61L 15/60* (2006.01)

(52) U.S. Cl.
  CPC .... *A61F 13/00068* (2013.01); *A61F 13/0253* (2013.01); *A61B 2046/205* (2016.02); *A61F 13/0206* (2013.01); *A61F 2013/00702* (2013.01); *A61L 15/425* (2013.01); *A61L 15/58* (2013.01); *A61L 15/60* (2013.01); *A61L 2300/404* (2013.01)

(56) References Cited

U.S. PATENT DOCUMENTS

| | | | | |
|---|---|---|---|---|
| 7,723,560 | B2* | 5/2010 | Lockwood | A61F 13/0259 602/45 |
| 8,212,100 | B2* | 7/2012 | Moore | A61F 13/0246 602/43 |
| 10,046,095 | B1 | 8/2018 | Middaugh | |
| 2005/0070835 | A1* | 3/2005 | Joshi | A61M 1/009 602/41 |
| 2007/0027414 | A1* | 2/2007 | Hoffman | A61M 1/0088 602/2 |
| 2007/0265586 | A1* | 11/2007 | Joshi | A61F 13/0216 604/313 |
| 2009/0299251 | A1* | 12/2009 | Buan | A61M 1/0088 602/43 |
| 2010/0292626 | A1* | 11/2010 | Gundersen | A61F 13/0203 602/56 |
| 2010/0324510 | A1 | 12/2010 | Andresen | |
| 2011/0028918 | A1* | 2/2011 | Hartwell | A61M 1/0088 604/319 |
| 2012/0234484 | A1* | 9/2012 | Takada | A61P 17/00 156/250 |
| 2014/0142526 | A1* | 5/2014 | Auguste | A61F 13/0206 604/365 |
| 2014/0249495 | A1* | 9/2014 | Mumby | A61F 13/0206 604/359 |
| 2014/0350494 | A1 | 11/2014 | Hartwell et al. | |
| 2015/0119831 | A1* | 4/2015 | Robinson | A61F 13/0216 604/319 |
| 2015/0245949 | A1 | 9/2015 | Locke et al. | |
| 2015/0320605 | A1* | 11/2015 | Pigg | A61F 13/15707 604/385.05 |
| 2016/0144084 | A1 | 5/2016 | Collinson | |
| 2017/0079846 | A1 | 5/2017 | Locke et al. | |
| 2017/0128642 | A1 | 5/2017 | Buan | |
| 2017/0367895 | A1 | 12/2017 | Holm et al. | |
| 2017/0367896 | A1 | 12/2017 | Holm et al. | |
| 2018/0021178 | A1 | 1/2018 | Locke et al. | |

OTHER PUBLICATIONS

International Search Report filed in PCT/U2019/048343 dated Nov. 21, 2019.
Medical Products Catalog, Coating and Converting Technologies, 2015.

* cited by examiner

DRESSING

BACKGROUND

Negative pressure is a term used to describe a pressure that is below normal atmospheric pressure. Known topical negative pressure devices range from cumbersome wrinkle reducing suction apparatuses to wound therapies that include fluid-permeable wound cavity filling elements, covering dressings, reasonably airtight means for sealing against the skin, and drainage tubes connecting the wound site and cavity filling element to the vacuum source via a fluid collection canister.

One type of dressing used with negative pressure includes a porous foam positioned on the wound and a dressing cover over the porous foam. The drainage tube connected with a pump siphons exudate from the wound after a water tight seal around the wound has been provided. Advancements can be made with regard to these dressings used with negative pressure

SUMMARY

In view of the foregoing, a dressing includes a drape, a pressure-sensitive acrylic-based adhesive on a skin-facing surface of the drape, an island of absorbent material, a silicone gel backing film, a silicone gel on the silicone gel backing film, and a release liner. The drape is a thin film capable of maintaining a negative pressure underneath the drape upon application of a vacuum. The island of absorbent material has a smaller area than the drape and is applied onto the skin-facing surface of the drape so as to leave a first margin of adhesive-coated drape around the island of absorbent material. The silicone gel backing film has a frame shape and a smaller footprint than the drape and a larger footprint than the island of absorbent material. The silicone gel backing film is affixed to the drape so as to leave a second margin of adhesive-coated drape around the silicone gel backing film. The silicone gel at least substantially matches the frame shape of the silicone gel backing film and surrounds the island of absorbent material while leaving the second margin of adhesive-coated drape around the silicone gel backing film. The release liner has a larger area than the drape. The release liner is coated with a fluorosilicone release coating on at least one side of the release liner. The fluorosilicone release coating is in contact with the pressure-sensitive acrylic-based adhesive in the second margin of the adhesive-coated drape and is in contact with the silicone gel.

The dressing mentioned above can further include a casting sheet, which is paper, and the drape is cast onto the casting sheet.

In any of the dressings mentioned above the drape can be a polyurethane film.

In any of the dressings mentioned above the absorbent material can include a superabsorbent polyester.

In any of the dressings mentioned above the silicone gel backing film can be a polyurethane, polyethylene, polypropylene or copolyester film.

In any of the dressings mentioned above the release liner can be a polyester film.

In any of the dressings mentioned above the drape can include a hole extending through the drape and surrounded by the silicone gel. In this embodiment, an air-permeable/liquid-impermeable filter can cover the hole. In this embodiment, the air-permeable/liquid-impermeable filter can be affixed to the skin-facing surface of the drape via the pressure-sensitive acrylic-based adhesive. Alternatively, the air-permeable/liquid-impermeable filter can be affixed to a surface of the drape that is opposite to the skin-facing surface. When the air-permeable/liquid-impermeable filter is affixed to the skin-facing surface of the drape via the pressure-sensitive acrylic-based adhesive, the air-permeable/liquid-impermeable filter is capable of sticking to acrylic adhesive.

The dressing(s) mentioned in the aforementioned paragraph can be combined with a vacuum source that is in fluid communication with the hole extending through the drape. The vacuum source can be a reactor configured to consume at least one gas found in air, e.g., oxygen or nitrogen.

A method of assembling a dressing includes forming a hole through a casting sheet and a drape formed on the casting sheet and applying an island of absorbent material onto a skin-facing surface of the drape. The skin-facing surface of the drape has a pressure-sensitive acrylic-based adhesive deposited thereon, and the island of absorbent material is applied leaving a first margin of adhesive-coated drape around the island of absorbent material. The method further includes applying a silicone gel backing film having a silicone gel deposited thereon onto the skin-facing surface of the drape so as to surround the island of absorbent material leaving a second margin of adhesive-coated drape around the silicone gel backing film. The method also includes providing a release liner coated with a fluorosilicone release coating in contact with the pressure-sensitive acrylic-based adhesive in the second margin of adhesive-coated drape and in contact with the silicone gel.

The method mentioned above can further include affixing an air-permeable/liquid-impermeable filter to the drape covering the hole. The method can further include kiss cutting the casting sheet around the island of absorbent material, and removing an inside portion of casting sheet.

DETAILED DESCRIPTION

The invention is not limited in its application to the details of construction and arrangement of components provided in the following description or illustrated in the attached drawings. The invention is capable of other embodiments and being practiced in various manners. The phraseology and terminology used herein is for the purpose of description and should not be regarded as limiting. Moreover, the use of "including," "comprising," or "having" and variations thereof is meant to encompass the items listed thereafter and equivalents thereof as well as additional items.

Figure 1:
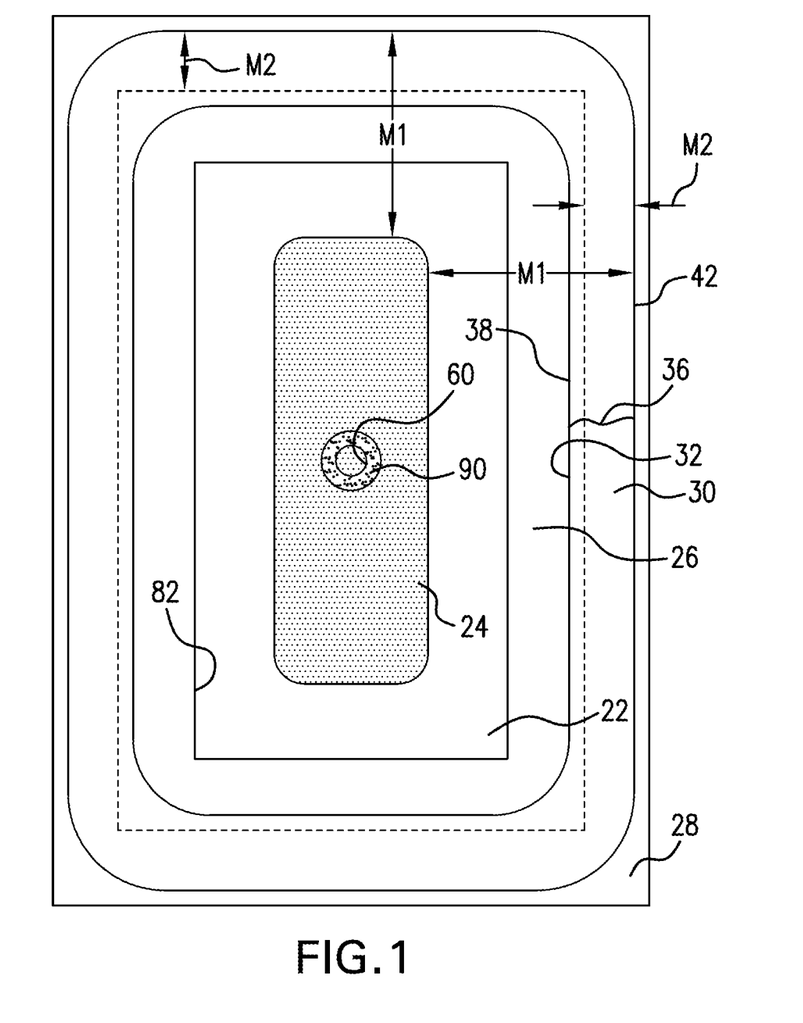
FIG. 1 is a schematic plan view of an example of a dressing.

The present disclosure generally relates to negative pressure-type wound dressings, but the dressings described herein need not always be used with negative pressure. FIG. 1 depicts an embodiment of a wound dressing that is useful to create a pressure that is below normal atmospheric pressure beneath the dressing 20. The dressing 20 generally includes a drape 22, an island of absorbent material 24, silicone gel 26, and a release liner 28. The arrangement of the components of the dressing 20 and the material from which the components are constructed facilitates conformity of the dressing around a wound, surgical incision, or other tissue site (hereinafter simply referred to as a "tissue site") so as to maintain a negative pressure environment beneath the drape 22 and around the tissue site for extended periods of time, and also allows easier handling for placement of the dressing onto the skin.

The drape 22 is a thin film capable of maintaining a negative pressure underneath the drape 22 upon application of a vacuum. The thin film from which the drape 22 is made can be substantially impermeable to liquids but somewhat permeable to water vapor, while still being capable of maintaining negative pressure underneath the drape. For example, the thin film material from which the drape 22 is made may be constructed of polyurethane or other semi-permeable material such as that sold under the Tegaderm® brand or 9834 TPU tape available from 3M. Similar films are also available from other manufacturers. Even though the film from which the drape 22 is made may have a water vapor transmission rate of about 836 g/m$^2$/day or more, these films are still capable of maintaining negative pressure underneath the drape 22 when an appropriate seal is made around the periphery of a tissue site.

The drape 22 can be cast onto a casting sheet 30, which can be made from paper. When the dressing 20 is assembled, the casting sheet 30 can be kiss cut to provide a casting sheet opening 32. The drape 22 can be made from a transparent material such that the island of absorbent material 24 and the silicone gel 26 can be visible within a "window" defined by the casting sheet opening 32 in the casting sheet 30. A cross cut 36 can extend from an internal side 38 of the casting sheet 30, after the material that defines the casting sheet opening 32 has been removed, to an outer side 42 of the casting sheet. Since the drape 22 is made from a very thin film, by providing a frame-like structure that is the casting sheet 30 connected with the drape 22, application of the dressing 20 is facilitated by way of providing a relatively stiffer or more rigid casting sheet 30 to grasp while placing the dressing 20 over the tissue site. After the dressing 20 has been placed, the casting sheet 30 can be grasped at the cross cut 36 and pulled towards a corner to remove the casting sheet 30 from the drape 22. As is evident in the embodiment depicted in FIG. 1, the casting sheet 30 is kiss cut around the area of the silicone gel 26 so as to allow for the person placing the dressing 20 onto the tissue site to see both the island of absorbent material 24 and the silicone gel 26 during placement of the dressing 20.

Figure 2:
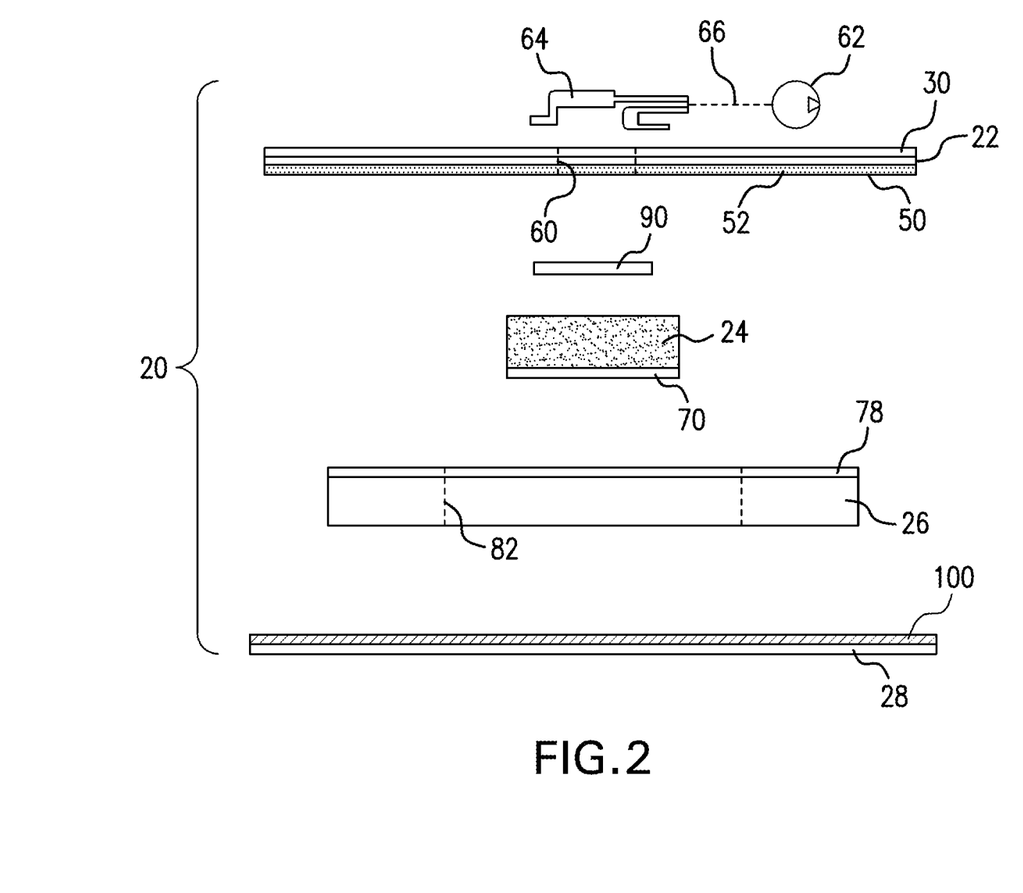
FIG. 2 is an exploded side view of the dressing depicted in FIG. 1.

With reference to FIG. 2, a pressure-sensitive acrylic-based adhesive 50 is applied on a skin-facing surface 52 of the drape 22. Other types of adhesives could be applied to the drape 22, however, a pressure-sensitive acrylic-based adhesive is known to provide strong initial tack that can last for a relatively long time, for example a few days, when in contact with the skin. The pressure-sensitive acrylic-based adhesive 50 can be applied over an entirety of the skin-facing surface 52 of the drape 22, which can also be useful to retain other components of the dressing 20 during assembly.

The drape 22 can also include an opening 60, which can allow for the connection of a vacuum source 62 to the dressing 20. The opening 60 can be cut through the casting sheet 30 (prior to removal of the portion of the casting sheet 30 which forms the casting sheet opening 32) and the drape 22 within an area surrounded by the silicone gel 26. A fitting 64 (schematically depicted in FIG. 2) can be placed over the opening 60 and connect to the vacuum source 62 via a hose 66 (also schematically depicted in FIG. 2).

The island of absorbent material 24 is applied onto the skin-facing surface 52 of the drape 22 and is affixed to the drape 22 via the pressure-sensitive acrylic-based adhesive 50. As more clearly seen in FIG. 1, the island of absorbent material 24 has a smaller area than the drape 22 so as to leave a first margin M1 of adhesive-coated drape around the island of absorbent material 24. The first margin M1 is shown as having a vertical and horizontal component in FIG. 1, which may or may not be equal to one another. The absorbent material from which the island of absorbent material 24 is made can be a super absorbent polyester. Examples of such absorbent materials include a hydroactive wound pad available under the trademark Vilmed®. With reference to FIG. 2, a silicone coating 70 can be provided on a skin-contacting side of the island of absorbent material 24, if desired, which is very compatible with skin and other tissue.

The silicone gel 26 is applied on a silicone gel backing film 78. The silicone gel backing film 78 can be a polyurethane, polyethylene, polypropylene, or co-polyester film, that is brought in contact with the skin-facing surface 52 of the drape 22 to fix the silicone gel 26 to the drape 22. Typically, silicone does not bond well to an acrylic-based adhesive and the pressure-sensitive acrylic-based adhesive 50 is applied to the drape 22 in the illustrated embodiment. By providing the silicone gel 26 on the silicone gel backing film 78, the silicone gel 26 can be fixed with respect to the drape 22 while still being able to utilize a pressure-sensitive acrylic-based adhesive 50 on the drape 22. This allows for the benefit of providing a silicone gel 26 with the dressing 20 that can contact the skin around the tissue site and provide a much better seal than only having the pressure-sensitive acrylic-based adhesive 50, which allows for negative pressure to be obtained underneath the drape 22 around the wound site.

The silicone gel 26 can operate as a sealing gasket for the dressing 20 to maintain negative pressure (with respect to atmosphere) underneath the dressing 20. When used for negative pressure wound therapy applications, it is desirable that the sealing gasket have the following functional characteristics: (1) the material from which the sealing gasket is made is extremely biocompatible, i.e., able to be worn for durations measured in days and weeks, with no discernible effects to the skin on which it resides, (2) the material should have mild adhesive properties, relative to skin, so that the material does not become unsealed as the wearer performs activities of daily living, and (3) the material should be flexible and conformable to adjust to the movements of the patient, while maintaining a "vacuum" seal at all times. Of the available biomedical materials, silicone gel is identified as a gasket candidate, such as the gel available from Polymer Science, Inc. as part number PS-1050. Other materials, such as hydrogel, could function as a sealing gasket but are not as biocompatible a silicone gel.

With reference back to FIG. 1, the silicone gel backing film 78 has a frame shape in that a central opening 82 is provided in the silicone gel backing film 78 so that the silicone gel backing film 78 and the silicone gel 26 surrounds the island of absorbent material 24. The silicone gel backing film 78 has a smaller footprint (outer dimension) than the drape 22 and a larger footprint than the island of absorbent material 24. As such, when the silicone gel backing film 78 is affixed to the drape 22 a second margin M2 of adhesive-coated drape is positioned around the silicone gel backing film. The silicone gel 26 is positioned on the silicone gel backing film 78 and at least substantially matches the frame shape of the silicone gel backing film 78 so as to surround the island of absorbent material 24 while leaving the second margin M2 of adhesive-coated drape around the silicone gel 26. This allows the second margin M2 of adhesive-coated drape to affix to the skin around the tissue site to hold the dressing 20 in place. Since pressure-sensitive acrylic-based adhesive is not particularly suitable for an airtight or watertight seal, the silicone gel 26 provides an adequate seal so that negative pressure can be maintained within a space beneath the drape 22 and surrounded by the silicone gel 26.

An air-permeable/liquid-impermeable filter 90 can be provided covering the opening 60 in the drape 22. As shown in FIGS. 1 and 2, the air-permeable/liquid-impermeable filter 90 is positioned against the skin-facing surface of the drape 22; however, the air-permeable/liquid-impermeable filter 90 can be provided on an outer surface of the drape 22. The air-permeable/liquid-impermeable filter 90 is made from a hydrophobic material such as expanded polytetrafluoroethylene (ePTFE). PTFE is known as being a difficult material to bond because it is "non-stick" by nature. Accordingly, other hydrophobic materials such as microporous membranes available from NXTNano LLC of Claremore, Okla., USA can be used for the air-permeable/liquid-impermeable filter 90. NXTNano LLC provides a microporous membrane constructed of nanofibers having a direct venting of 0.4 cfm while maintaining 14,000 mm hydrostatic head. The NXTNano LLC material is a thermoplastic polyurethane, which makes it easier to affix to the drape 22 via the pressure-sensitive acrylic-based adhesive 50 on the skin-facing surface 52 of the drape 22.

The release liner 28 contacts the drape 22 along the second margin M2 of the adhesive-coated drape and along with the silicone gel 26. The release liner 28 also contacts the island of absorbent material 24 and more particularly the silicone coating 70 on the island of absorbent material 24. As such, the release liner 28 should work well with both an acrylic-based adhesive and a silicone gel. Oftentimes, release liners are coated with a silicone coating; however, silicone coatings often are not compatible with silicone gel which can result in the silicone gel being pulled along with the release liner 28 when the release liner 28 is removed from the drape 22 and other components of the dressing 20.

In the illustrated example, the release liner 28 is coated with a fluorosilicone release coating 100 on the side of the release liner 28 that contacts the pressure-sensitive acrylic-based adhesive 50 on the drape 22 and the appropriate surfaces of the silicone gel 26 and the island of absorbent material 24. The release liner 28 can be a polyester film coated on one side with the fluorosilicone release coating 100, which can be used with silicone adhesives. This release coating 100 is also compatible with the pressure-sensitive acrylic-based adhesive 50 on the skin-facing surface of the drape 22 such as that available with 9834 TPU tape available from 3M. The release liner 28 has a larger area than the drape 22 and is removed from the drape 22 prior to the drape being affixed to a patient's skin around the wound site.

Figure 3:
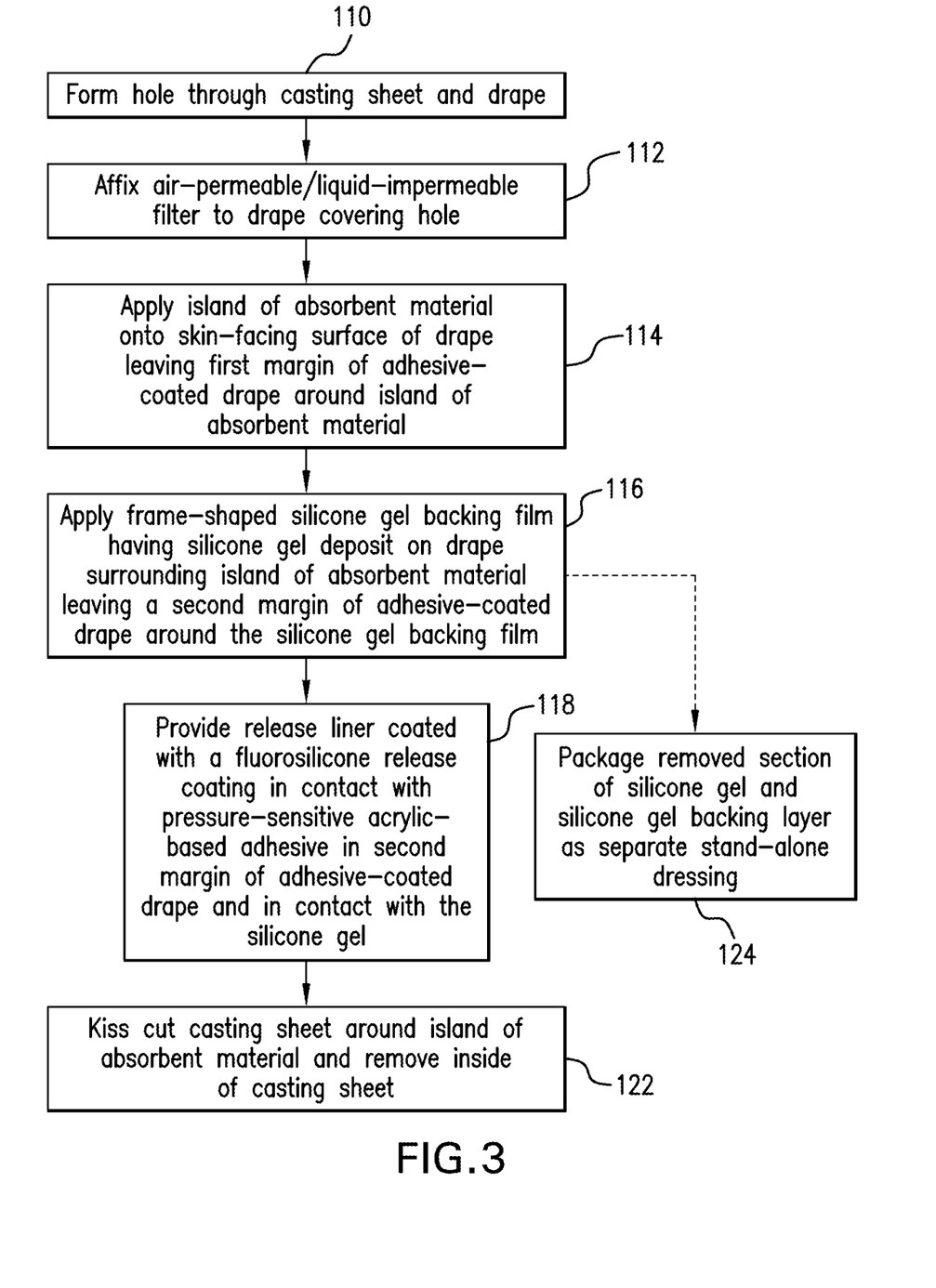
FIG. 3 is a flow diagram depicting an example of a process of assembling the dressing depicted in FIG. 1.

A method of assembling a dressing will be described with reference to the flow diagram shown in FIG. 3 and the embodiment of the dressing shown in FIGS. 1 and 2. The method of assembling the dressing, however, is not limited to only the embodiment of the dressing 20 shown in FIGS. 1 and 2, nor is it limited to the particular order in which the steps are described or shown in FIG. 3, unless otherwise specifically mentioned.

For example, the casting sheet 30 and the drape 22 can be provided as a pre-manufactured roll that is provided on a converter and, at 110, the opening 60 can be formed through the casting sheet 30 and the drape 22. The opening 60 can be punched or cut through the casting sheet 30 and the drape 22, or provided in another manner.

At 112, the air-permeable/liquid-impermeable filter 90 is affixed to the drape 22 covering the opening 60. The air-permeable/liquid-impermeable filter 90 can be affixed to the skin-facing surface 52 of the drape 22 via the pressure-sensitive acrylic-based adhesive 50. Alternatively, the air-permeable/liquid-impermeable filter 90 can be affixed to the surface of the drape 22 that is opposite to the skin-facing surface 52.

At 114, the island of absorbent material 24 is applied onto the skin-facing surface 52 of the drape 22. The skin-facing surface 52 of the drape 22 has the pressure-sensitive acrylic-based adhesive 50 deposited thereon. As such, the island of absorbent material 24 sticks to the skin-facing surface 52 of the drape 22 leaving the first margin M1 of adhesive-coated drape around the island of absorbent material 24.

At 116, the silicone gel backing film 78 having the silicone gel 26 deposited thereon is applied onto the skin-facing surface 52 of the drape 22 so as to surround the island of absorbent material 24 leaving the second margin M2 of adhesive-coated drape around the silicone gel backing film 78. As discussed above, silicone does not typically adhere to an acrylic-based adhesive. As such, the silicone gel backing film 78, which can be made from a polyurethane, polyethylene, polypropylene or copolyester film, is provided having the silicone gel 26 deposited thereon so that the silicone gel 26 is fixed to the drape 22.

At 118, the release liner 28 coated with the fluorosilicone release coating 100 is provided so as to contact the pressure-sensitive acrylic-based adhesive 50 in the second margin M2 of the adhesive-coated drape and is also in contact with the silicone gel 26. The fluorosilicone release coating 100 is specially formulated so as to release from both the pressure-sensitive acrylic-based adhesive 50 and the silicone gel 26.

At 122, the casting sheet 30 is kiss cut around the island of absorbent material 24 to provide the central opening 82. An inside portion of the casting sheet 30 is removed, which forms the central opening 82 that can act as a sort of window. The drape 22 is manufactured from a transparent thin film, which allows the operator placing the dressing 20 on the tissue site the ability to view the tissue site while placing the dressing.

As mentioned above, the silicone gel 26 is applied on a silicone gel backing film 78, and the silicone gel backing film 78 has a frame shape in that a central opening 82 is provided in the silicone gel backing film 78 so that the silicone gel backing film 78 and the silicone gel 26 surrounds the island of absorbent material 24. To form the central opening 82, the silicone gel 26 and the silicone gel backing film 78 can be cut and removed from the remainder that makes up the frame shape. At 124, this removed section of the silicone gel 26 and the silicone gel backing film 78 can be packaged as a separate stand-alone dressing. Such a dressing can be useful to cover an incision site as an occlusive dressing that is not under negative pressure or can be used for other applications.

Figure 4:
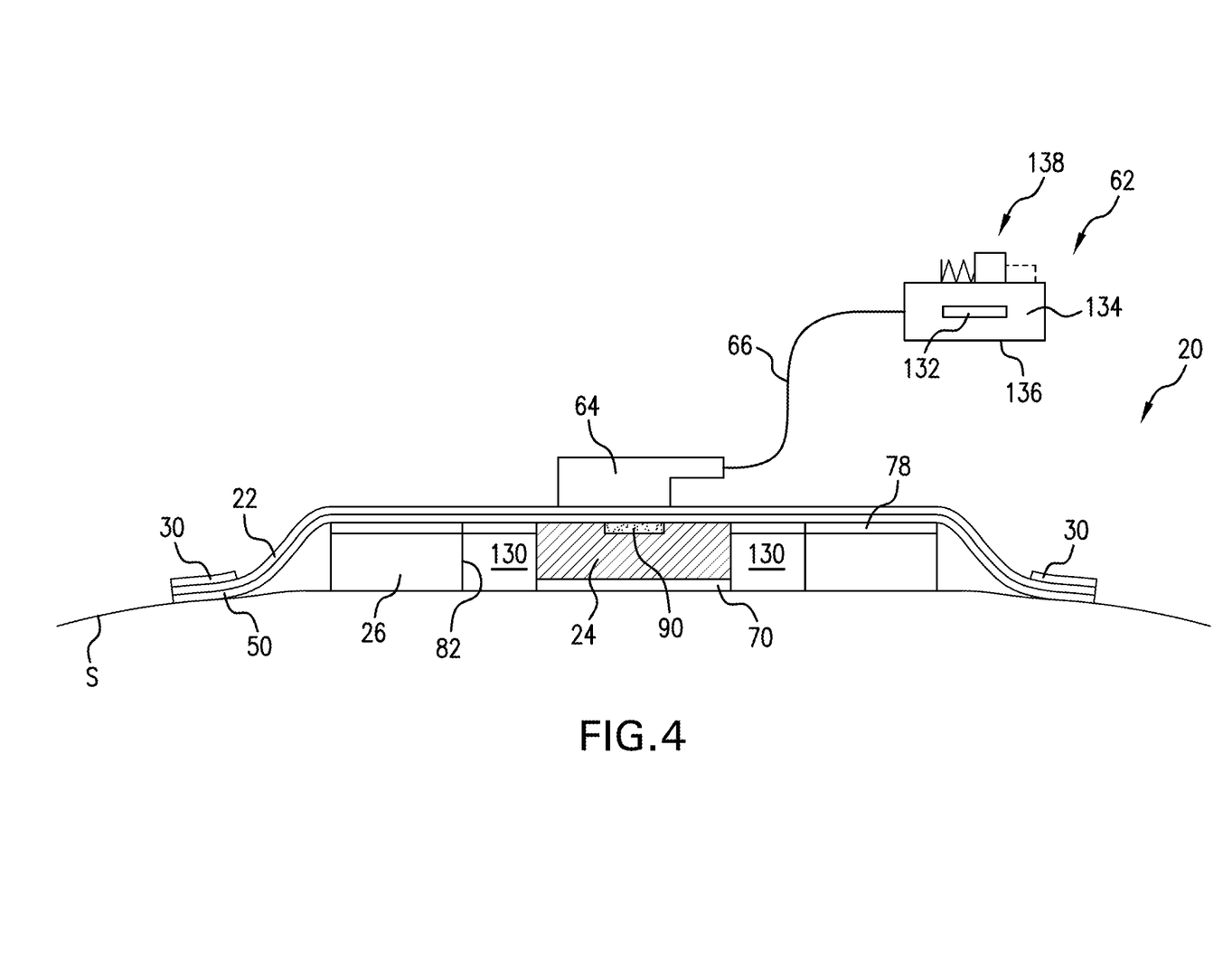
FIG. 4 is a schematic cross-sectional view of the dressing placed on skin around a tissue site.

With reference to FIG. 4, in use the dressing 20 is applied to the skin S around a tissue site with the pressure-sensitive acrylic-based adhesive 50 in contact with the skin S. The drape 22 can be brought in contact with the skin S with the casting sheet 30 with the central opening 82 formed therein still attached to the drape 22. The casting sheet 30 can then be grasped near the cross cut 36 and removed from the drape 22. When the drape 22 is brought against the skin S, the silicone gel 26 surrounds the tissue site to define an enclosed volume 130, which is beneath the drape 22 and surrounded by the silicone gel 26. The vacuum source 62 is in communication with the opening 60 provided through the drape 22 to provide pneumatic communication between the vacuum source 62 and the enclosed volume 130.

The vacuum source 62 can include a reactor 132 or similar chemical pump that is configured to react with gasses found in air to remove these gasses from air. For example, the reactor 132 can be an oxygen scavenger which removes oxygen from the air within the enclosed volume 130 so as to reduce the gas pressure within the enclosed volume by approximately 20%. Since the vacuum source 62 in this embodiment includes a chemical pump, any leakage around the enclosed volume 130 is important to prevent. The ingress of outside oxygen, which could use up the reactor 132 in the vacuum source 62, should be prevented from penetrating either through the drape 22 or the silicone gel 26 or between the silicone gel 26 and the skin S.

In FIG. 4, the reactor 132 is positioned in a closed chamber 134 that is in fluid communication with the enclosed volume 130 beneath the drape 22 and surrounded by the silicone gel 26 when the dressing 20 is affixed to skin S around the tissue site. The closed chamber 134, which can be defined by a housing 136, and/or the enclosed volume 130 communicates with ambient only when a pressure differential between the closed chamber 134 and/or the enclosed volume 130 and atmosphere exceeds a predetermined threshold relative to standard atmospheric pressure. This is in contrast to known negative pressure systems which employ a mechanical pump that draws air from an enclosed volume through the mechanical pump into ambient. Leakage in these systems is not as critical since the mechanical pump typically can overcome the effect of a relatively small flow of air entering the enclosed volume by way of leakage in the system. In contrast, too much leakage when using the reactor 132 may result in the reactor 132 being consumed and no longer able to scavenge oxygen (or other gases found in air). As such, the closed chamber 134 and/or the enclosed volume 130 communicates with ambient only when the pressure differential relative to standard atmospheric pressure between the closed chamber 134 and/or the enclosed volume 130 and atmosphere exceeds a predetermined threshold, which can be between −80 mm Hg to −150 mm Hg.

A relief valve 138 can be provided on the housing 136 and or in communication with the closed chamber 134. The relief valve 138 can be set to open to allow for communication between ambient and the closed chamber 134 when the pressure differential exceeds −150 mm Hg, for example where the pressure in the enclosed volume 130 is below about 610 mm Hg where atmospheric pressure is about 760 mm Hg. This can be relevant when the enclosed volume 130 is initially drawn down to a relative negative pressure, e.g., a pressure less than about 760 mm Hg, through the use of a mechanical pump or other mechanism and the closed chamber 134 and reactor 132 are later connected with the enclosed volume 130 through the fitting 64. If the reactor 132 and the closed chamber 134 are connected with the enclosed volume 130 when the enclosed volume 130 is at a pressure below atmospheric pressure while air (having 20% oxygen) is in the enclosed volume 130, as the oxygen is removed from the enclosed volume, the pressure may drop below 610 mm Hg, which might be undesirable in some situations. Accordingly, the relief valve 138 can be provided.

The silicone gel 26 provides a better seal than simply acrylic-based adhesive alone. Nevertheless, silicone gels and adhesives typically do not work well together in that the silicone gel typically does not adhere to the acrylic-based adhesive. As such, the silicone gel backing film 78 can be provided between the silicone gel 26 and the pressure-sensitive acrylic-based adhesive 50 on the skin-facing surface of the drape 22 to allow the silicone gel backing film 78 to be fixed with respect to the drape 22.

Moreover, the release liner 28 (visible in FIGS. 1 and 2) is removed from the skin-facing surface 52 of the drape 22 prior to the drape 22 being brought into contact with the skin S. As mentioned above, the release liner 28 is coated with the fluorosilicone release coating 100 that is suitable for removal from the pressure-sensitive acrylic-based adhesive 50 on the skin-facing surface of the drape 22 as well as removal from the silicone gel 26 and the silicone coating 70 on the island of absorbent material 24.

As mentioned above, the island of absorbent material 24 is provided within the enclosed volume 130 when the dressing 20 is affixed to the skin S around the tissue site. Additionally, the air-permeable/liquid-impermeable filter 90 can be provided to cover the opening 60 and the drape 22 so as to prevent the migration of fluid, e.g., exudate, from the island of absorbent material 24 out of the dressing 20 toward the vacuum source 62.

A dressing and a process for manufacturing a dressing have been described above with particularity. Modifications and alterations will occur to those upon reading and understanding the preceding detailed description. The invention, however, is not limited to only the embodiments described above. Instead, the invention is broadly defined by the appended claims and the equivalents thereof. It will be appreciated that various of the above-disclosed embodiments and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A method of assembling a dressing comprising:
   forming a hole through a casting sheet and a drape formed on the casting sheet;
   applying an island of absorbent material onto a skin-facing surface of the drape, wherein the skin-facing surface of the drape has a pressure-sensitive acrylic-based adhesive deposited thereon, leaving a first margin of adhesive-coated drape around the island of absorbent material; and
   applying a silicone gel backing film having a silicone gel deposited thereon onto the skin-facing surface of the drape so as to surround the island of absorbent material leaving a second margin of adhesive-coated drape around the silicone gel backing film.

2. The method of claim 1, further comprising:
   affixing an air-permeable/liquid-impermeable filter to the drape covering the hole.

3. The method of claim 1, further comprising:
   kiss cutting the casting sheet around the island of absorbent material; and
   removing an inside portion of casting sheet.

4. A method of assembling a dressing comprising:
   providing a casting sheet and a thin film drape as a pre-manufactured roll;
   forming a hole through the casting sheet and the drape;
   applying an island of absorbent material onto a skin-facing surface of the drape, wherein the skin-facing surface of the drape has a pressure-sensitive acrylic-based adhesive deposited thereon, leaving a first margin of adhesive-coated drape around the island of absorbent material; and applying a silicone gel backing film having a silicone gel deposited thereon onto the skin-facing surface of the drape so as to surround the island of absorbent material leaving a second margin of adhesive-coated drape around the silicone gel backing film.

* * * * *